US008656638B2

(12) United States Patent
Stevenson et al.

(10) Patent No.: US 8,656,638 B2
(45) Date of Patent: Feb. 25, 2014

(54) COMPOUNDS AND PROCESSES THAT GENERATE CYCLOPROPENES AND SUBSTITUTED CYCLOPROPENES ON DEMAND

(76) Inventors: Cheryl D. Stevenson, Bloomington, IL (US); John Perrin Davis, Bloomington, IL (US)

( * ) Notice: Subject to any disclaimer, the term of this patent is extended or adjusted under 35 U.S.C. 154(b) by 336 days.

(21) Appl. No.: 13/065,521

(22) Filed: Mar. 23, 2011

(65) Prior Publication Data

US 2011/0232178 A1 Sep. 29, 2011

Related U.S. Application Data

(60) Provisional application No. 61/341,014, filed on Mar. 25, 2010, provisional application No. 61/462,572, filed on Feb. 4, 2011.

(51) Int. Cl.

| | |
|---|---|
| ***A01N 3/00*** | (2006.01) |
| ***A01N 43/20*** | (2006.01) |
| ***C07D 305/14*** | (2006.01) |
| ***C07C 1/207*** | (2006.01) |

(52) U.S. Cl.

CPC ............ *C07D 305/14* (2013.01); *C07C 1/2078* (2013.01); *A01N 3/00* (2013.01)

USPC ..................................... 47/58.1 LS; 549/328

(58) Field of Classification Search

CPC ....... A01N 3/00; A01N 43/20; C07D 305/14; C07C 1/2078

USPC ..................................... 549/328; 47/58.1 LS

See application file for complete search history.

(56) References Cited

PUBLICATIONS

Pandya and Thorpe (J. Chem. Soc., Transactions (1923), vol. 123; p. 2852-2865).*

Photochemical Conversions of 3H-Pyrazoles to Cyclopropenes and 1,2-Diazabicyclo-[2.1.0] pent-2-enes. G. L. Gloss, W. A. Boll, H. Heyn, and V. Dev J. Am. Chem. Soc. 1968, 90, 173-178.

The Photodecomposition of Butyrolactone in the Vapor Phase. R. Simonaitis, and J. N. Pitts, Jr. J. Phys. Chem. 1971, 75, 2333-2337.

Cyclobutadiene. O. L. Chapman, C. L. McIntosh, J. Pacansky J. Am. Chem. Soc. 1973, 95, 614-617.

Single-Crystal X-ray Structure of 1,3-Dimethylcyclobutadiene by Confinement in a Crystalline Matrix. Yves-Marie Legrand, Arie van der Lee, and Mihail Barboiu Science 2010, 329, 299-302.

The Gas-Phase Thermal and Photochemical Decomposition of Heterocyclic Compounds Containing Nitrogen, Oxygen, or Sulfur. Silvia Braslavsky, and Julian Heicklen Chemical Reviews 1977, 77, 473-511.

Comment on "Single-Crystal X-ray Structure of 1,3-Dimethylcyclobutadiene by Confinement in a Crystalline Matrix"Igor V. Alabugin, Brian Gold, Michael Shatruk, and Kirill Kovnir Science 2010, 330, 1047-1048.

Palladium-Catalyzed [3+2] Cycloaddition of Carbon Dioxide and Trimethylenemethane under Mild Conditions. George E. Greco,* Brittany L. Gleason, Tiffany A. Lowery, Matthew J. Kier, Lisa B. Hollander, Shoshanah A. Gibbs, and Amanda D. Worthy Org. Let. 2007, 9, 3817-3820.

From Small Rings to Big Things: Fruit Ripening, Floral Display and Cyclopropenes. Brian Halton Chemistry in New Zealand, Jan. 2009, 34-37.

Transition Structures of the Ene Reactions of Cyclopropene. Qiaolin Deng, Bert E. Thomas IV, K. N. Houk, and Paul Dowd J. Am. Chem. Soc. 1997, 119, 6902-6908.

The Palladium Chloride Catalyzed Cyclodimerization of 1-Methylcyclopropene. F. J. Weigert, R. L. Baird, and J. R. Shapley J. Am. Chem. Soc. 1970, 92, 6630-6635.

Cyclobutanone from Methylenecyclopropane via Oxaspiropentane. J. R. Salaun, J. Champion, and J. M. Conia Organic Syntheses, Coll. vol. 6, 1988, p. 320; vol. 57, 1977, p. 36.

[2+2] Cycloadditions by Oxidative Visible Light Photocatalysis. Michael A. Ischay, Zhan Lu, and Tehshik P. Yoon J. Am. Chem. Soc., 2010, 132, 8572-8574.

Cyclopropene. V. Some Reactions of Cyclopropene. Kenneth B. Wiberg, William J. Bartley J. Am. Chem. Soc., 1960, 82, 6375-6380.

Synthesis of 1-Methylcyclopropene. Farley Fisher, Douglas E. Applequist J. Org. Chem., 1965, 30, 2089-2090.

An Efficient and Convenient Synthesis of I-Methylcyclopropene. Ronald M. Magid, Thomas C. Clarke, and Charles D. Duncan J. Org. Chem., 1971, 36, 1320-1321.

1-Methylcyclopropene, A Novel Gaseous Inhibitor of Ethylene Action, Improves the Life of Fruits, Cut Flowers, and Potted Plants. M. Serek, E. C. Sisler, and M. S. Reid Acta Horticulturae 1995, 394, 337-345.

Consecutive Photolyses of Naphthalenedicarboxylic Anhydrides in Low Temperature Matrixes: Experimental and Computational Studies on Naphthynes and Benzocyclopentadienylideneketenes. Tadatake Sato, Hiroyuki Niino, and Akira Yabe J. Phys. Chem. A 2001, 105, 7790-7798.

Diastereomerenreine 1,2-Cyclopropandicarbonsauren und Derivate. Wolfgang von der Seal, Robert Reinhardt, Hubert-Matthias Seidenspinner, Josef Stawitz und Helmut Quast Liebigs Ann. Chem. 1989, 703-712.

Ketene Formation in Benzdiyne Chemistry: Ring Cleavage versus Wolff Rearrangement. Tadatake Sato, Hiroyuki Niino, and Akira Yabe J. Am. Chem. Soc. 2003, 125, 11936-11941.

Three-membered Rings. The Preparation of Some 1,2-Cyclopropanedicarboxylic Acids. Layton L. McCoy J. Am. Chem. Soc. 1958, 80, 6568-6572.

(Continued)

*Primary Examiner* — Noble Jarrell
*Assistant Examiner* — Valerie Rodriguez-Garcia
(74) *Attorney, Agent, or Firm* — Fenningham, Stevens and Dempster LLP; David P. Fitzgibbon, Esq.

(57) ABSTRACT

Compounds and methods that release 1-methylcyclopropene, 1-trifluoromethylcyclopropene, and other substituted cyclopropenes are disclosed. The compounds are of the class of chemical analogue of 2-oxa-bicyclo[2.1.0]penta-3-one useful as vessels for molecular plant ethylene receptor inhibitors. The compounds and methods overcome present limitations for storage, transportation, and application of the cyclopropene containing compounds by using light, including sunlight, and/or heat as the primary release trigger. Additional products released include innocuous gases and value added aryl-group compounds.

7 Claims, 5 Drawing Sheets

(56) References Cited

PUBLICATIONS

Three-membered Rings. N. Solvent Control for the Stereoselective Formation of Cyclopropanes Substituted at Two of the Ring Carbons. Layton L. McCoy J. Am. Chem. Soc. 1962, 84, 2246-2249.
Decarbonylation Studies in the endo- and exo-Tricyclo[3.2.1.02-4]octen-8-one Series. Stereoelectronic Requirements for Cyclopropyl Participation. Brian Halton, Merle A. Battistel Rolf Rehberg, Cynthia L. Deyrup, and Michael E. Brennan J. Am. Chem. Soc. 1967, 89, 5964-5965.
Thermal Isomerization of 3,6-Dideuterio- and 1,2,7,8,9,9-Hexadeuterio-cis-bicyclic[6.1.0]-nona-2,4,6-triene. John E. Baldwin, A. Harry Andrist, and Robert K. and Pinschmidt, Jr. J. Am. Chem. Soc. 1972, 94, 5845-5851.
Naphthalene Diels-Alder in a Self-Assembled Molecular Flask. Takashi Murase, Shinnosuke Horiuchi, and Makoto Fujita J. Am. Chem. Soc. 2010, 132, 2866-2867.
Photochemical Conversions of 3H-Pyrazoles to Cyclopropenes and 1,2-Diazabicyclo-[2.1.0] pent-2-enes. G. L. Closs, W. A. Boll, H. Heyn, and V. Dev J. Am. Chem. Soc. 1968, 90, 173-178.
Photosensitized Decarbonylation of Furans. R. Srinivasan J. Am. Chem. Soc. 1967, 89, 1758-1758.
Photochemistry of Methylfurans. Selectivities of Ring Contraction Reactions. H. Hiraoka J. Phys. Chem. 1970, 74, 574-581.
Ketene Formation in Benzdiyne Chemistry: Ring Cleavage versus Wolff Rearrangement. Sato, T.; Nino, H.; Yabe, A. J. Am. Chem. Soc. 2003, 125, 11936-11941.
The Formation of Cyclopentadienones. Depuy, C. H.; Isaks, M.; Eilers, K. L.; Morris, G. F. J. Org. Chem. 1964, 29, 3503-3507.
Role of ethylene receptors during senescence and ripening in horticultural crops. Gaurav Agarwal, Divya Choudhary, Virendra P. Singh and Ajay Arora Plant Signaling and Behavior, 7:7, 827-846, Jul. 2012.

* cited by examiner

COMPOUNDS AND PROCESSES THAT GENERATE CYCLOPROPENES AND SUBSTITUTED CYCLOPROPENES ON DEMAND

CROSS-REFERENCE

Provisional Patent Applications covering the below described invention were submitted, via Express Mail, which bore label number EM 425754569 US and EG 835094455 US, and were assigned application Nos. 61/341,014 and 61/462,572. The inventors claim the priority date of said Provisional Patent Applications.

GOVERNMENT RIGHTS

Not Applicable.

BACKGROUND

The useful properties of plant ethylene receptor inhibitors have been well documented. For example, 1-methylcyclopropene (CAS #3100-04-7), a substituted cyclopropene (hereafter, simply referred to as "1-MCP"), has been demonstrated to help increase the shelf life and storage characteristics of many fruits and flowers.

More recently, it has been demonstrated that 1-MCP, or analogues thereof, can be used in agricultural applications. Specifically, 1-MCP, and analogues thereof, are used to retard the ripening process in plants, which allows the plant materials to last much longer than untreated plants. Additionally, 1-MCP, and analogues thereof, are used for crop protection during times of stress that includes drought, excessive heat, and excessively low temperatures. With regard to the above specified agricultural applications and without limitation, the 1-MCP analogue compounds may be considered to be related compounds which have similar uses as 1-MCP in agricultural applications. The analogues of 1-MCP with regard to the above specified agricultural applications involve compounds which contain the cyclopropene moiety. The compounds cyclopropene, 3-methylcyclopropene, 1-ethylcyclopropene, 1,2-dimethylcyclopropene, 1,3-dimethylcyclopropene, and 3,3-dimethylcyclopropene have similar agricultural significance, albeit the aforementioned compounds are weaker plant ethylene receptor inhibitors in comparison to 1-MCP, and they are included amongst many other releasable analogue compounds that are covered by this technology. Generally, these cyclopropene containing compounds are regarded as plant ethylene receptor antagonist, and inhibit plant senescence and abscission in a wide variety of plant species. In particular, the cyclopropene containing analogue 1-trifluoromethylcyclopropene (hereafter, simply referred to as "1-TFMCP") is a plant ethylene receptor antagonist with different characteristics than 1-MCP which include slightly increased water solubility and increased penetration through waxy or otherwise lipophilic layers of some plant species.

Unfortunately, 1-MCP and 1-TFMCP are highly unstable gases, and so cannot be conventionally applied, or easily stored for long periods of time. Presently, the only commercially available forms of 1-MCP are in highly dilute mixtures and 1-TFMCP is not commercially available. For the foregoing reasons, there is a need for a solution to the problems associated with the shelf-life, long term storage, transport, and release of 1-MCP, 1-TFMCP, and additional cyclopropene containing analogues.

SUMMARY

The above listed applicants have identified a solution to the problems associated with the shelf-life, long term storage, transport, and release of 1-MCP, 1-TFMCP, and analogues thereof, on an as needed basis by covalently linking 1-MCP, 1-TFMCP, or analogues thereof, directly to a molecular compound which, upon activation, releases the compound 1-methylcyclopropene, 1-TFMCP, or analogues thereof. Additionally, some compounds that are used in this manner to release 1-MCP may be further stabilized via a reversible reaction forming a ketal (as an asymmetric ortho-ester), which only requires exposure to a mildly acidic aqueous solution to afford deprotection, thereby yielding the immediate light and/or heat active precursor compound and either a diol or two equivalents of an alcohol. The light and/or heat active precursor may then yield the cyclopropene or substituted cyclopropene (such as 1-MCP, 1-TFMCP, etc.) upon further exposure to light and/or heat. This technology allows for formulations that include solid mixtures, aqueous solutions, non-aqueous solutions, colloidal dispersions, or direct application of the release vent such that the 1-MCP Release System can be conventionally applied, which is then activated by light and/or heat to release the 1-MCP, 1-TFMCP, or analogue thereof.

DRAWINGS

These and other features, aspects and advantages of the present invention will become better understood with reference to the following description, appended claims and accompanying drawings where:

Figure 4:
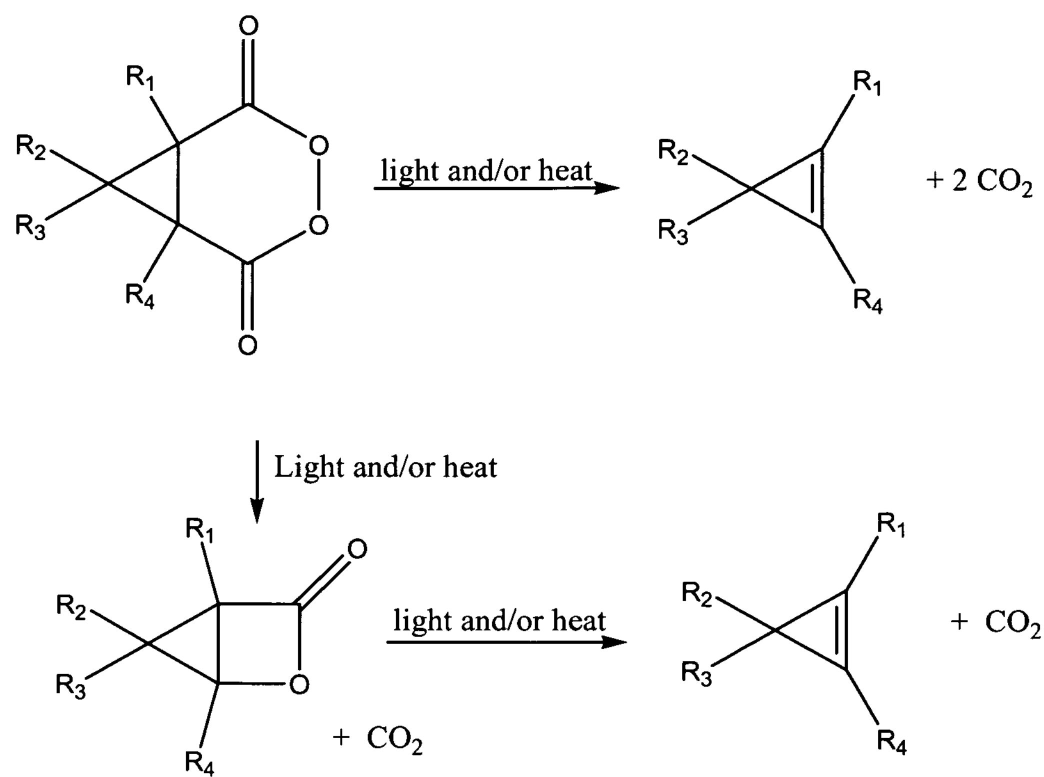
Figure 5:
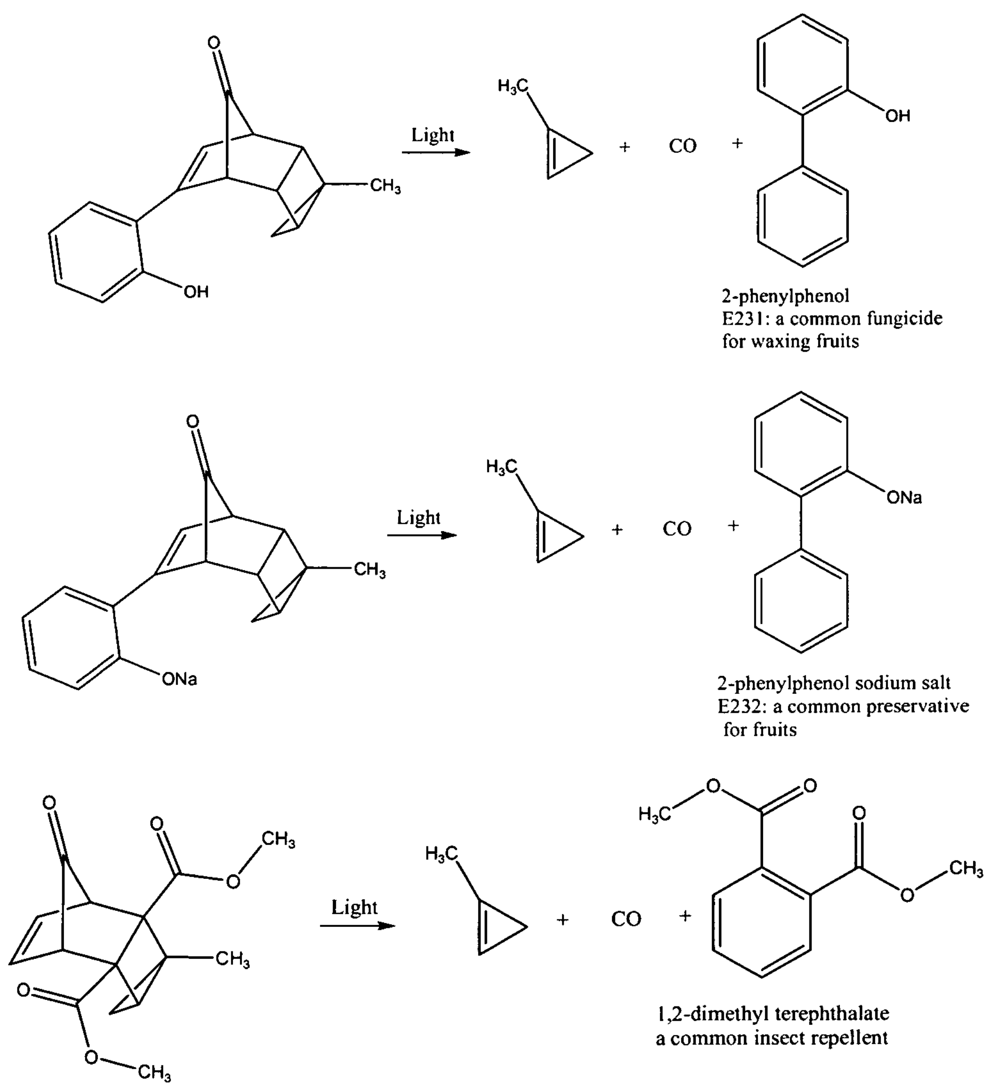

FIG. 4 shows the manner by which 3,4-dioxa-bicyclo[4.1.0]hepta-2,5-dione may proceed through a stable intermediate comprising 2-oxa-bicyclo[2.1.0]penta-3-one in a multi-step reaction scheme ultimately resulting in the generation of 1-MCP or analogues thereof from 3,4-dioxa-bicyclo[4.1.0]hepta-2,5-dione; and FIG. 5 shows some possibilities of value added aryl-unit containing products that may be created from different configurations of Compound 4.

DESCRIPTION

The strategies discussed herein pertaining to the capture and release, and to release without capture of 1-MCP, 1-TFMCP, and analogues thereof, are based upon light and/or heat driven release mechanisms. When the covalently linked system is exposed to light and/or heat, 1-MCP, 1-TFMCP, or analogue thereof, is released along with the linked molecule. The release system formulations include one, or more, of such 1-MCP, 1-TFMCP, or other analogue releasing compounds, and in various proportions or mixtures thereof. Here, the term mixtures includes, but is not limited to, combinations of compounds within a given method (described herein), combinations of compounds spanning one or more methods (described herein), combinations of stereo-isomers, where they exist, and all permutations thereof, and also where any of the methods contained herein are used in combination with a different method in the general field of practice.

In addition to light, heat may also be used to generate the desired 1-MCP, 1-TFMCP, or related analogue in some cases. Thus, light, heat, or combinations of light and heat may be used in these reactions to generate the desired compounds. The amount of heat and/or light energy required for the release of 1-MCP, 1-TFMCP, or analogues thereof, is dependent upon the specific precursor compound and the specific formulation in which it is contained, amongst other determinants. Thus, the heat and light energy requirements for the release of 1-MCP, 1-TFMCP, or analogues thereof, can be attenuated to meet a desired release profile. Specific compounds more generally represented by Markush Structures of Compounds 1 through 8 can be obtained such that very high thermal stability is imparted, but a low light energy threshold is obtained. In the aforementioned example, the compound will exhibit long shelf life, even at high temperatures, so long as exposure light is avoided during storage. Upon exposure to light, the 1-MCP, 1-TFMCP, or analogue thereof is released.

Some of the precursor compounds (such as Compound 1) used to generate 1-MCP, 1-TFMCP, or analogues thereof, may be further stabilized as their respective ketal (as an asymmetric ortho-ester), which affords increased stability to heat and/or light. Upon exposure of such compounds to acidic aqueous solutions under mild conditions, the immediate precursor is generated along with the respective diol or two equivalents of an alcohol containing compound. The immediate precursor will then yield 1-MCP, 1-TFMCP, or analogues thereof, and carbon dioxide upon further exposure to heat and/or light.

Without limitation, the 1-MCP Release System more fully set forth below is comprised of a precursor molecule (Compound 1 through 8), which upon activation to an excited state, generates 1-MCP, 1-TFMCP, or analogue thereof, and one or more by-products. The by-product(s) may consist of one or more gases. In addition, the by-product(s) may also entail the release of an additional molecule which contains an aryl group. The aryl group released may be, by design, a "value added material." By way of example and without limitation, such value added material(s) may be a pesticide (such as a herbicide, insecticide, fungicide, rodenticide, and/or acaracide), herbicide, bee attractant, or preservative.

To date the below identified molecules and protocols have been identified as addressing the problems associated with the capture and release, and release without capture of 1-MCP, 1-TFMCP, or analogues thereof. These aforementioned molecules are referred to as Compounds 1 through 8, and the aforementioned methods are referred to as Methods 1 through 4 in the context of this patent application.

The 1-MCP and analogues thereof, may be described as two general sets of reaction products which contain a cyclopropene moiety. These two product sets can be represented as Product 1 or Product 2, below, with respect to the methods detailed more fully herein.

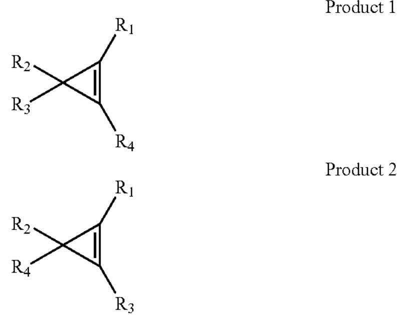

Where $R_1$ or $R_4$ of Product 1 is comprised of a methyl group (—$CH_3$), and all other $R_1$ through $R_4$ are hydrogens, Product 1 will be 1-MCP, below. Where $R_1$ or $R_3$ of Product 2 is comprised of a methyl group (—$CH_3$), and all other $R_1$ through $R_4$ are hydrogens, Product 2 will be 1-MCP, below. Where $R_1$ or $R_4$ of Product 1 is comprised of a tri-fluoromethyl group (—$CF_3$), and all other $R_1$ through $R_4$ are hydrogens, Product 1 will be 1-TFMCP, below. Where $R_1$ or $R_3$ of Product 2 is comprised of a tri-fluoromethyl group (—$CF_3$), and all other $R_1$ through $R_4$ are hydrogens, Product 2 will be 1-TFMCP, below.

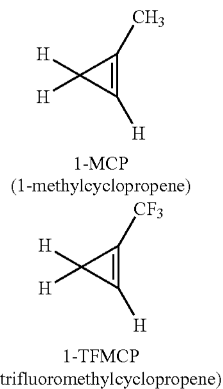

1-MCP (1-methylcyclopropene)

1-TFMCP (1-trifluoromethylcyclopropene)

Compound 1: Analogues of 2-oxa-bicyclo[2.1.0]penta-3-one

Compound 1 (analogues of cyclopropane annulated beta-lactone), which may also be referred to as analogues of 2-oxa-bicyclo[2.1.0]penta-3-one, below, has been found to be reactive in strategies to generate 1-MCP, and analogues thereof, by heat and/or light.

Compound 1

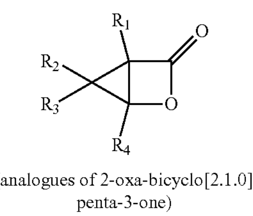

(analogues of 2-oxa-bicyclo[2.1.0] penta-3-one)

Figure 1:
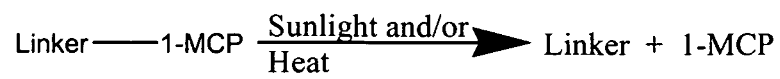
FIG. 1 shows the general light and/or heat driven release mechanism contemplated herein.
Figure 2:
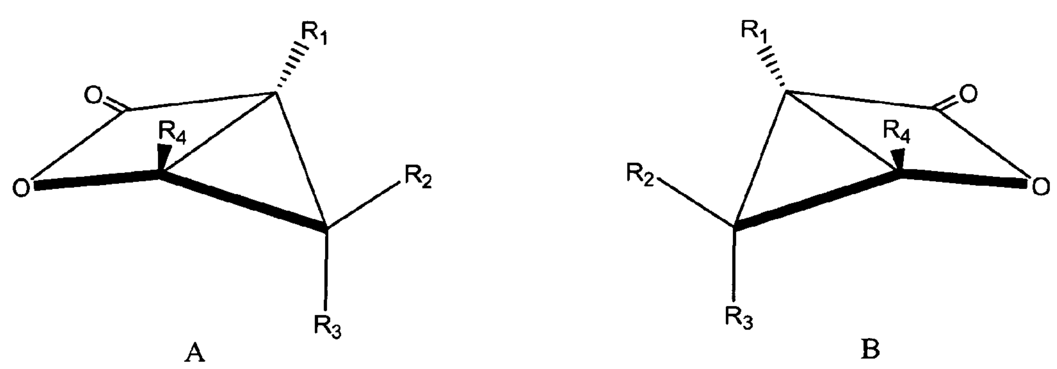
FIG. 2 shows the general stereochemistry of 2-oxa-bicyclo[2.1.0]penta-3-one.

The general stereochemistry of Compound 1 may be more clearly seen in FIG. 2, where A and B represent the two general enantiomers of Compound 1, where they exist.

The general reaction of Compound 1 upon exposure to light and/or heat, depending on the composition of the identified R groups, yields Product 1, above, where the R groups of Product 1 correspond to the same substituents on Compound 1, and one equivalent of carbon dioxide. Sunlight, or artificial light sources may be used. Increased rates may be obtained by using sonication (ultrasound) and/or a LASER as the source of light and/or in conjunction with a photo-catalyst, such as one comprising palladium. The product entailing Product 1 in this case will generally be an achiral product or a racemic mixture where they exist. It is possible to obtain a non-racemic product composition by this method under certain conditions, such as when the light source is polarized.

The R groups for Compound 1 may, independently for each respective $R_1$ through $R_4$, be comprised of a hydrogen (—H), chlorine (—Cl), or fluorine (—F) atom, or group comprised of methyl (—$CH_3$), ethyl (—$CH_2CH_3$), ethylene (—$CHCH_2$), ethyne (—CCH), n-propyl (—$CH_2CH_2CH_3$), iso-propyl (—$CH(CH_3)_2$), cyclopropyl (—$CH(CH_2)_2$), tert-butyl (—$C(CH_3)_3$), propene (—$CHCHCH_3$ or —$CH_2CHCH_2$), cyclopropene (—$CH(CH)_2$ or —$C(CH)CH_2$), propyne (—$CCCH_3$ or —$CH_2CCH$), hydroxyl (—OH), methylalcohol (—$CH_2OH$), ethylalcohol (—$CH_2CH_2OH$ or —$CH(OH)CH_3$), ethyldiol (—$CH(OH)CH_2(OH)$), propanol (—$CH(OH)CH_2CH_3$ or —$CH_2CH(OH)CH_3$ or —$CH_2CH_2CH_2OH$), propandiol (—$CH(OH)CH(OH)CH_3$ or —$CH(OH)CH_2CH_2OH$ or —$CH_2CH(OH)CH_2OH$), methylether (—$OCH_3$), ethylether (—$OCH_2CH_3$), fluoromethyl (—$CH_2F$), difluoromethyl (—$CHF_2$), trifluoromethyl (—$CF_3$), fluoroethyl (—$CFHCH_3$ or —$CH_2CH_2F$), perfluoroethyl (—$CF_2CF_3$), fluoropropyl (—$CHFCH_2CH_3$ or —$CH_2CHFCH_3$ or —$CH_2CH_2CH_2F$) perfluoropropyl (—$CF_2CF_2CF_3$ or —$CF(CF_2)_2$), chloromethyl (—$CH_2Cl$), dichloromethyl (—$CHCl_2$), trichloromethyl (—$CCl_3$), chloroethyl (—$CClHCH_3$ or —$CH_2CH_2Cl$), perchloroethyl (—$CCl_2CCl_3$), chloropropyl (—$CHClCH_2CH_3$ or —$CH_2CHClCH_3$ or —$CH_2CH_2CH_2Cl$), perchloropropyl (—$CCl_2CCl_2CCl_3$ or —$CCl(CCl_2)_2$), cyano (—CN), aldehyde (—C(O)H), carboxylic acid (—C(O)OH), carboxylate (—$C(O)O^-$), carbomethoxy (—$C(O)OCH_3$), carboethoxy (—$C(O)OCH_2CH_3$), dimethyl amine (—$N(CH_3)_2$), or acid chloride (—C(O)Cl).

The products of 1-MCP and carbon dioxide may be obtained from either enantiomer of Compound 1 when $R_1$ or $R_4$ is a methyl group and all other R groups are hydrogen. The products of 1-TFMCP and carbon dioxide may be obtained from either enatiomer of Compound 1 when $R_1$ or $R_4$ is a trifluoromethyl group and all other R groups are hydrogen.

Compound 2: Analogues of 2-oxa-bicyclo[2.1.0]penta-3-one ketal

The Compound 1 may be generated via a reversible reaction from its respective analogue ketal (an asymmetric ortho-ester), identified below as Compound 2 (analogues of 2-oxa-bicyclo[2.1.0]penta-3-one ketal). Here, the $R_1$, $R_2$, $R_3$, and $R_4$ groups may be independently comprised of any of the R groups discussed above for Compound 1. The $R_5$ and $R_6$ groups may share a covalent bond (shown as a dashed line, below) or may be two independent subunits. Independently, for $R_5$ and $R_6$, they may be comprised of a methyl (—$CH_3$), ethyl (—$CH_2CH_3$), or propyl (—$CH_2CH_2CH_3$) groups. Where $R_5$ and $R_6$ share a covalent bond, $R_5$ and $R_6$ together may be an ethyl (—$CH_2CH_2$—) or propyl (—$CH(CH_3)CH_2$—) group.

Compound 2

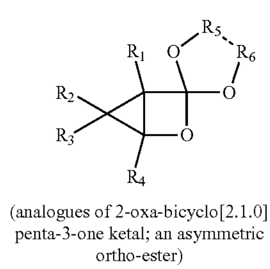

(analogues of 2-oxa-bicyclo[2.1.0] penta-3-one ketal; an asymmetric ortho-ester)

A general reaction to form the ketal protected variant of Compound 1 (as an asymmetric ortho-ester; Compound 2), utilizes the light initiated [2+2] reaction of Product 1 (now, as a reactant) with a dimethyl carbonate, diethyl carbonate, ethylene carbonate, or propylene carbonate. The reaction can be carried out in a wide variety of solvent media (excepting acidic aqueous solutions), or under vacuum conditions for the gas-phase reaction. The use of the above molecules in a photo-induced [2+2] reaction yields Compound 2, where $R_5$ and $R_6$ are both methyl (—$CH_3$) or ethyl (—$CH_2CH_3$) for the case where dimethyl carbonate, or diethyl carbonate are used, respectively, and yields Compound 2 where $R_5$ and $R_6$ share an ethylene bridge (—$CH_2CH_2$—) for the case that ethylene carbonate is used, or share a methyl substituted ethylene bridge (—$CH(CH_3)CH_2$—) for the case that propylene carbonate is used.

When $R_1$ or $R_4$ is a methyl group on Product 1 (1-MCP), and all other R groups are hydrogens, 1-MCP may be sequestered by a photo-induced [2+2] reaction with the aforementioned carbonates. Such a reaction yields Compound 2 where $R_1$ is a methyl group and $R_2$, $R_3$, and $R_4$ are hydrogens, or Compound 2 where $R_4$ is a methyl group and $R_1$, $R_2$, and $R_3$ are hydrogens. When $R_1$ or $R_4$ is a trifluoromethyl group on Product 1 (1-TFMCP), and all other R groups are hydrogens, 1-TFMCP may be sequestered by a photo-induced [2+2] reaction with the aforementioned carbonates. Such a reaction yields Compound 2 where $R_1$ is a trifluoromethyl group and $R_2$, $R_3$, and $R_4$ are hydrogens, or Compound 2 where $R_4$ is a trifluoromethyl group and $R_1$, $R_2$, and $R_3$ are hydrogens.

Upon exposure of Compound 2 to excess water in the presence of $H^+$ (an aqueous acidic solution), the following respective alcohol or diol (as Product 3, below) and Compound 1 are generated under mild conditions.

Product 3

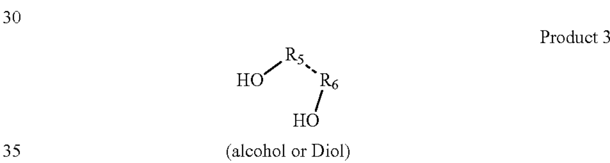

(alcohol or Diol)

Compound 3: Analogues of 3,4-dioxa-bicyclo[4.1.0]hepta-2,5-dione

Another important molecule is Compound 3 below, (analogues of 3,4-dioxa-bicyclo[4.1.0]hepta-2,5-dione). Here, the $R_1$, $R_2$, $R_3$, and $R_4$ groups may be independently comprised of any of the R groups discussed above for Compound 1.

Compound 3

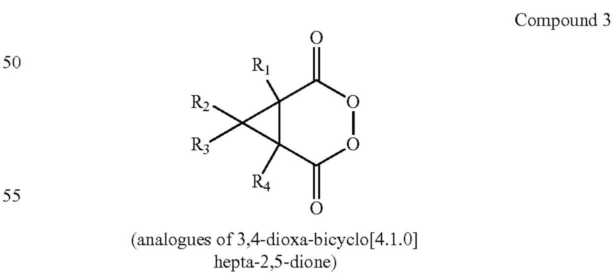

(analogues of 3,4-dioxa-bicyclo[4.1.0] hepta-2,5-dione)

Figure 3:
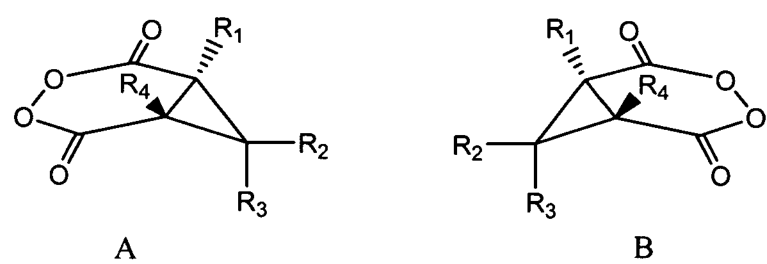
FIG. 3 shows the general stereochemistry of 3,4-dioxa-bicyclo[4.1.0]hepta-2,5-dione.

The general stereochemistry for Compound 3 is illustrated in FIG. 3, where A and B represent the two general stereoisomers. Both enantiomers of Compound 3, where they exist, are active in generating Product 1.

The general reaction for Compound 3 to produce cyclopropenes and substituted cyclopropenes (as Product 1, above) requires the exposure of Compound 3 to light and/or heat and generates products consisting of Product 1, where $R_1$ through $R_4$ of Compound 3 correspond to $R_1$ through $R_4$ of Product 1, and two equivalents of carbon dioxide. Sunlight, or artificial light sources may be used. Increased rates may be obtained by using sonication (ultrasound) and/or a LASER as the source of light and/or a light source in conjunction with a photo-catalyst, such as one comprising palladium.

For the case that 1-MCP is to be generated from Compound 3, $R_1$ or $R_4$ is comprised of a methyl group and all other R groups are hydrogens and upon exposure to light and/or heat 1-MCP and two equivalents of $CO_2$ are produced. For the case that 1-TFMCP is to be generated from Compound 3, $R_1$ or $R_4$ is comprised of a trifluoromethyl group and all other R groups are hydrogens and upon exposure to light and/or heat 1-TFMCP and two equivalents of $CO_2$ are produced.

In addition, when subject to light and/or heat Compound 3 may proceed through a stable intermediate comprising Compound 1 in a multi-step reaction scheme ultimately resulting in the generation of 1-MCP or analogues thereof (Product 1) from Compound 3 as illustrated in FIG. 4.

Compound 4: Analogues of tetracyclo[$5.2.1.0^{2,6}.0^{3,5}$]deca-8-en-10-one

Another important molecule is Compound 4, below, (analogues of tetracyclo[$5.2.1.0^{2,6}.0^{3,5}$]deca-8-en-10-one).

Compound 4

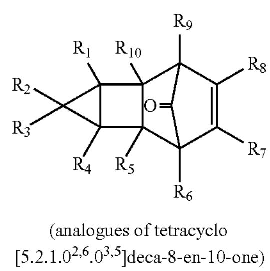

(analogues of tetracyclo [$5.2.1.0^{2,6}.0^{3,5}$]deca-8-en-10-one)

Here, the $R_1$ or $R_4$ must be comprised of a methyl group (—$CH_3$), or a trifluoromethyl group (—$CF_3$) and all other $R_1$ through $R_4$ are protons (—H). Both the $R_1$ and $R_4$ groups of Compound 4 are in an eclipsed (cis) conformation, as are the $R_5$ and $R_{10}$ groups. The $R_5$ through $R_{10}$ groups may, independently, be comprised of any of the groups discussed, above, for Compound 1. Additionally, any of the $R_5$ through $R_{10}$ groups may, independently, be comprised of a phenyl (—C6H5), a sodium phenoxide (—C6H4ONa), or a substituted phenyl group where the substituents (five total substituents including protons) on the phenyl group may be any of the groups discussed above for Compound 1. It is preferable that at least one of $R_5$ through $R_{10}$ be comprised of something other than hydrogen.

There are several analogues of Compound 4, which may be represented by the Markush Structures, below, where the primary difference between the respective compounds pertains to their endo, and/or exo orientations. These orientations are (endo, endo), (endo, exo), (exo, exo), and (exo, endo) for the parent tetracyclo[$5.2.1.0^{2,6}.0^{3,5}$]deca-8-en-10-one compounds, below, Compound 4A, Compound 4B, Compound 4C, and Compound 4D, respectively, where bond angles have been distorted for labeling purposes. Due to steric hindrance effects, Compound 4B and Compound 4D generally exhibit greater stability than Compound 4A and Compound 4C, but any of the isomers and stereoisomers of Compounds 4A through 4D are suitable for producing Product 1 upon exposure to light or to light and heat.

Compound 4A

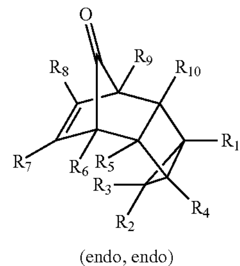

(endo, endo)

Compound 4B

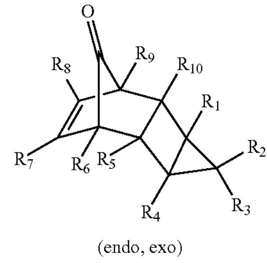

(endo, exo)

Compound 4C

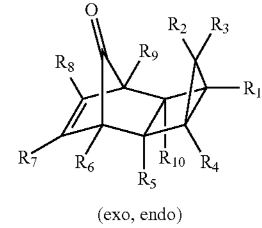

(exo, endo)

Compound 4D

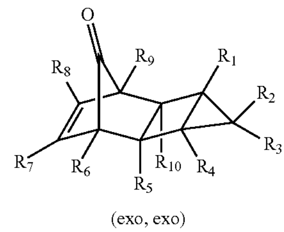

(exo, exo)

When Compound 4 is exposed to light or light and heat it yields one equivalent each of carbon monoxide, Product 1 as 1-MCP (if $R_1$ or $R_4$ is a methyl group) or 1-TFMCP (if $R_1$ or $R_4$ is a trifluoromethyl group), and Product 4 (below). Sunlight or artificial light sources may be used. Increased rates may be obtained by using sonication (ultrasound) and/or a LASER as the source of light and/or a light source in conjunction with a photo-catalyst, such as one comprising palladium.

Product 4

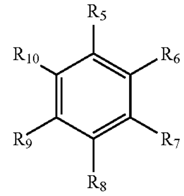

For the case where any one of $R_5$, $R_6$, $R_7$, $R_8$, $R_9$, or $R_{10}$ is a methyl ester (and all remaining R groups are protons) the light activated released compounds will be carbon monoxide, and either 1-MCP (where $R_1$ or $R_4$ is a methyl group) or 1-TFMCP (where $R_1$ or $R_4$ is a trifluoromethyl group), and methylbenzoate as Product 4 (a common bee attractant).

Similarly, amongst other possibilities, the aromatic system can be chosen to be a fungicide, preservative agent, or insect repellant as is the case for the released aromatic compounds depicted in FIG. 4. The list of potential "value added" aryl-unit containing products (as Product 4) afforded by Compound 4 are numerous. Many common pesticides (including herbicides, insecticides, fungicides, rodenticides, and/or acaracides, by way of example), bee attractant, preservative and other agrichemical compounds have been identified that are potential "value added" side products (as Product 4) of Compound 4 concomitant with the release of 1-MCP or 1-TFMCP.

Compound 5: Analogues of tricyclo[3.2.2.0$^{2,4}$]nona-6,8-diene

Another important molecule is Compound 5, below, (analogues of tricyclo[3.2.2.0$^{2,4}$]nona-6,8-diene), where bond angles are shown distorted for labeling purposes ($R_1$ and $R_4$ are in an eclipsed (cis) conformation).

Compound 5

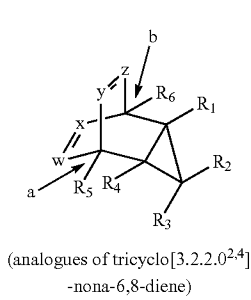

(analogues of tricyclo[3.2.2.0$^{2,4}$]-nona-6,8-diene)

Here, the convention of using "w" and "x" components represent the adjacent carbon atoms of the general substituents containing an ethylene bridge or aromatic ring which may or may not contain a silyl diether; A, B and C, respectively, below, where dashed lines (on A, B, and C) are used to indicate the covalent bonds to the bridgehead carbons of Compound 5 (indicated with arrows "a" and "b" for "w" and "x", respectively). The "y" and "z" components, likewise represent the adjacent carbon atoms of the same general substituents A, B and C, where "y" replaces "w" and "z" replaces "x" in each of A, B, and C, and they are now denoted as A', B' and C' and their corresponding R groups are now denoted as $R_n$'. In this manner, the six (non-equivalent) general permutations for Compound 5 can be expressed as AA', AB', AC', BB', BC', and CC'.

A

B

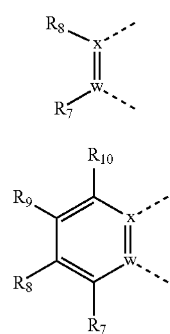

-continued

C

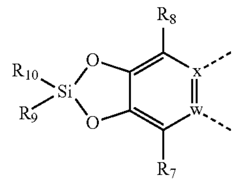

As an example, the Compound represented by 5AB' is shown below, where the w, x, y, and z labels have been removed.

Compound 5AB′

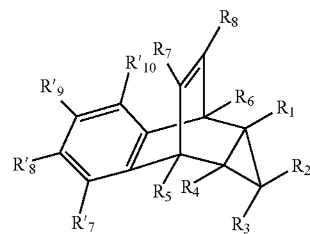

Here, the $R_1$ or $R_4$ must be comprised of a methyl group ($—CH_3$), or a trifluoromethyl group ($—CF_3$) and all other $R_1$ through $R_4$ are protons ($—H$). All other R and R' groups of Compound 5 may be comprised of any of the substituents under Compound 1.

When Compound 5 is exposed to heat, one equivalent each of Product 1 and Product 5, below, are yielded. Where $R_1$ or $R_4$ is a methyl group ($—CH_3$) and all other $R_1$ through $R_4$ are hydrogens, the Product 1 component will be 1-MCP. Where $R_1$ or $R_4$ is a trifluoromethyl group ($—CF_3$) and all other $R_1$ through $R_4$ are hydrogen, the Product 5 component will be 1-TFMCP. Akin to the Compound 4 and analogues thereof, all R groups beyond $R_1$ through $R_4$ should be chosen to entail the release of a benign or beneficial compound containing an aromatic moiety (instead of benzene, in the case of Compound 5AA'). Again, the list of potential "value-added" compounds is quite large. Where Compound 5AA' is used, and any one of $R_5$, $R_6$, $R_7$, $R_8$, $R_7'$, or $R_8'$ is comprised of a methyl ester group, and all other $R_5$ through $R_8'$ are hydrogens, the yielded product will contain (as Product 5AA') a methylbenzoate (a common bee attractant). Sonication (ultrasound) can be used to increase rates.

Product 5

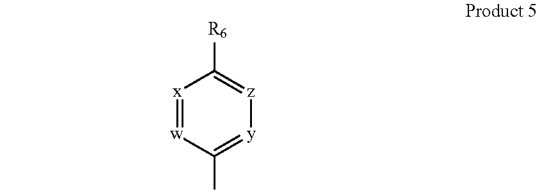

Method 1. Release of 1-MCP Via Exposure of 2(5H)-furanone & 2(3H)-furanone and Analogues Thereof to Light Under Method 1, Compound 6 (analogues of 2(5H)-furanone) and Compound 7 (analogues of 2(3H)-furanone), below, may be used to convey the general compounds that when exposed to light and/or heat release 1-MCP, or analogues thereof, as Product 1 and/or Product 2 in addition to one equivalent of carbon dioxide. The reaction pathway may involve a proton migration and bond shift such that Product 1 or Product 2 may be produced, depending upon the substituents (and wavelength of light utilized). The intermediate in this reaction is thought to involve Compound 1. Where Product 1 or Product 2 is to be comprised of 1-MCP, it is preferable that for both Compound 6 and Compound 7, $R_3$ or $R_4$ is comprised of a methyl group, and all other R are protons. Where Product 1 or Product 2 is to be comprised of 1-TFMCP, it is preferable that for both Compound 6 and Compound 7, $R_3$ or $R_4$ is comprised of a trifluoromethyl group, and all other R are protons. It is also preferred that the solution media used (if any) be transparent with a low cut-off absorption. Sunlight or artificial light sources may be used. Increased rates may be obtained by using sonication (ultrasound) and/or a LASER as the source of light and/or a light source in conjunction with a photo-catalyst, such as one comprising palladium.

Compound 6

Compound 7

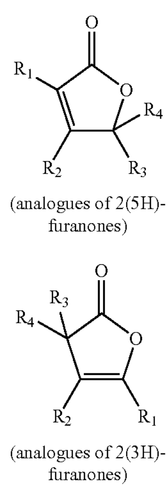

Each R group for Compound 6 and Compound 7 may be comprised of any of the R groups discussed for Compound 1.

When exposed to light in the ultra-violet Compound 6 yields one equivalent of product comprised of Product 1 and/or Product 2 and one equivalent of carbon dioxide. When exposed to light in the ultraviolet range Compound 7 yields one equivalent of product comprised of Product 1 and/or Product 2, and one equivalent of carbon dioxide. Where $R_4$ or $R_3$ of Compound 6 is comprised of a methyl group and all other R are protons, Compound 6 yields one equivalent of 1-MCP (as Product 1 or Product 2) and one equivalent of carbon dioxide under ideal conditions when exposed to a light source. Where $R_4$ or $R_3$ of Compound 6 is comprised of a trifluoro-methyl group and all other R are protons, Compound 6 yields one equivalent of 1-TFMCP (as Product 1 or Product 2) and one equivalent of carbon dioxide under ideal conditions when exposed to a light source.

Where $R_4$ or $R_3$ of Compound 7 is comprised of a methyl group and all other R are protons, Compound 7 yields one equivalent of 1-MCP (as Product 1 or Product 2) and one equivalent of carbon dioxide under ideal conditions when exposed to a light source. Where $R_4$ or $R_3$ of Compound 7 is comprised of a trifluoromethyl group and all other R are protons, Compound 7 yields one equivalent of 1-TFMCP (as Product 1 or Product 2) and one equivalent of carbon dioxide under ideal conditions when exposed to a light source.

Sunlight or artificial light sources may be used. Increased rates may be obtained by using sonication (ultrasound) and/or a LASER as the source of light and/or a light source in conjunction with a photo-catalyst, such as one comprising palladium.

Method 2: Release of 1-MCP Via Exposure of Analogues of 3-oxabicyclo[3.1.0]hexane-2,4-dione to Light Under Method 2, Compound 8 (analogues of 3-oxabicyclo [3.1.0]hexane-2,4-dione), below, may be used to convey the general compounds that when exposed to light release 1-MCP, or analogues thereof. Compound 8, when exposed to light, yields one equivalent each of Product 1, carbon dioxide, and carbon monoxide. For the case that $R_1$ or $R_4$ are comprised of a methyl group and all other R are protons in Compound 8, the yielded products will be one equivalent each of 1-MCP (as Product 1), carbon dioxide, and carbon monoxide. For the case that $R_1$ or $R_4$ are comprised of a trifluoromethyl group and all other R are protons in Compound 8, the yielded products will be one equivalent each of 1-TFMCP (as Product 1), carbon dioxide, and carbon monoxide.

Sunlight or artificial light sources may be used, but it is preferred that a high intensity light source in the ultraviolet range be used. Increased rates may be obtained by using sonication (ultrasound) and/or a LASER as the source of light and/or a light source in conjunction with a photo-catalyst, such as one comprising palladium.

Compound 8

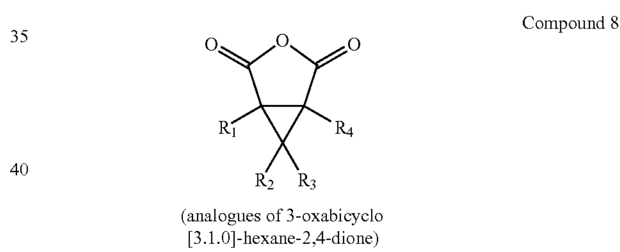

Each of the R groups identified for Method 2 may be comprised, independently for each, of any of the groups discussed for Compound 1.

Method 3: Release of 1-MCP and a Value Added Compound via Exposure of Analogues of tetracyclo $[5.2.1.0^{2,6}.0^{3,5}]$deca-8-en-10-one to Light or Light and Heat The representative parent compound for Method 3 which releases 1-MCP (as Product 1), carbon monoxide, and an Aromatic functionality containing by-product (as Product 4) may be illustrated by Compound 4 and its analogues identified above where $R_1$ or $R_4$ are comprised of a methyl group and all other $R_1$ through $R_4$ are protons. The representative parent compound for Method 3 which releases 1-TFMCP (as Product 1), carbon monoxide, and an Aromatic functionality containing by-product (as Product 4) may be illustrated by Compound 4 and its analogues identified above where $R_1$ or $R_4$ are comprised of a trifluoromethyl group and all other $R_1$ through $R_4$ are protons. The general reaction of Compound 4 upon exposure to light or to light and heat is one equivalent each of carbon monoxide, Product 1, and Product 4. Where any one of $R_5$ through $R_{10}$ are comprised of a methylester group and all other $R_5$ through $R_{10}$ are protons, the Product 4 component will be methylbenzoate (a common bee attractant). All other $R_1$ besides $R_1$ through $R_4$ may be any of the substituents discussed for Compound 1, above. Again, there are several analogues of the parent compound, which may be represented by Compounds 4A, 4B, 4C, and 4D, above, where the primary difference between the respective compounds pertains to their endo, and/or exo orientations.

The general reaction involving Compound 4 begins with a loss of carbon monoxide concomitant with bond shift and bond cleavage resulting in the loss of carbon monoxide, which may be initiated by either heat or light. The second reaction step entails a retro[2+2] reaction to form Product 1 and Product 4, which is initiated by light absorbance, and is driven by the formation of an aromatic Product 4. Sunlight or artificial light sources may be used. Increased rates may be obtained by using sonication (ultrasound) and/or a LASER as the source of light and/or a light source in conjunction with a photo-catalyst, such as one comprising palladium.

With respect to Product 4, proper substitution at positions $R_5$ through $R_{10}$ can lead to the release of benign, or even of beneficial compounds. By way of example and without limitation, the aromatic system can be chosen to be a fungicide, preservative agent, or insect repellant as is the case for the released aromatic compounds depicted in FIG. 4. The list of potential "value added" aryl-unit containing products (Product 4) afforded by Compound 4 are numerous. Many common pesticides (including herbicides, insecticides, fungicides, rodenticides, and/or acaracides, by way of example), bee attractant, preservative and other agrichemical compounds have been identified that are potential "value added" side products (as Product 4) of Compound 4 concomitant with the release of 1-MCP or 1-TFMCP.

Method 4: Release of 1-MCP and a Value Added Compound Via Exposure of Analogues of tricyclo[3.2.2.0$^{2,4}$]nona-6,8-diene to Heat The representative parent compound for Method 4 which upon exposure to heat releases 1-MCP (as Product 1), and an Aromatic functionality containing by-product (as Product 5) may be illustrated by Compound 5 and its analogues identified above where $R_1$ or $R_4$ are comprised of a methyl group and all other $R_1$ through $R_4$ are protons. The representative parent compound for Method 4 which upon exposure to heat releases 1-TFMCP (as Product 1), and an Aromatic functionality containing by-product (as Product 5) may be illustrated by Compound 5 and its analogues identified above where $R_1$ or $R_4$ are comprised of a trifluoromethyl group and all other $R_1$ through $R_4$ are protons. Where Compound 5AA' is used, and any one of $R_5$, $R_6$, $R_7$, $R_8$, $R_7$', or $R_8$' is comprised of a methyl ester group, and all other $R_5$ through $R_8$' are hydrogens, the yielded product will contain (as Product 5AA') a methylbenzoate (a common bee attractant). Sonication (ultrasound) can be used to increase rates. The general reaction of Compound 5 upon exposure to heat is the release of one equivalent each of Product 1 and Product 5. Furthermore, as outlined above each R, excepting $R_1$ through $R_4$, a substituent as discussed for Compound 1, above. Increased rates may be obtained by using sonication (ultrasound).

Akin to the Compound 4, and analogues thereof, R besides $R_1$ through $R_4$, should be chosen to entail the release of a benign or beneficial compound containing an aromatic moiety as Product 5 (instead of benzene). Again, the list of potential "value-added" compounds is quite large.

It will be understood that various changes can be made in the form details, arrangement, and proportions of the various parts without departing from the spirit and scope of the present invention.

The invention claimed is:

1. A compound of the formula:

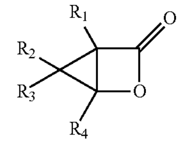

wherein:

$R_1$ is hydrogen (—H), chlorine (—Cl), or fluorine (—F) atom, a group consisting of methyl (—$CH_3$), ethyl (—$CH_2CH_3$), ethylene (—$CHCH_2$), ethyne (—CCH), n-propyl (—$CH_2CH_2CH_3$), iso-propyl (—$CH(CH_3)_2$), cyclopropyl (—$CH(CH_2)_2$), tert-butyl (—$C(CH_3)_3$), propene (—$CHCHCH_3$ or —$CH_2CHCH_2$), cyclopropene (—$CH(CH)_2$ or —$C(CH)CH_2$), propyne (—$CCCH_3$ or —$CH_2CCH$), hydroxyl (—OH), methylalcohol (—$CH_2OH$), ethylalcohol (—$CH_2CH_2OH$ or —$CH(OH)CH_3$), ethyldiol (—$CH(OH)CH_2(OH)$), propanol (—$CH(OH)CH_2CH_3$ or —$CH_2CH(OH)CH_3$ or —$CH_2CH_2CH_2OH$), propandiol (—$CH(OH)CH(OH)CH_3$ or —$CH(OH)CH_2CH_2OH$ or —$CH_2CH(OH)CH_2OH$), methylether (—$OCH_3$), ethylether (—$OCH_2CH_3$), fluoromethyl (—$CH_2F$), difluoromethyl (—$CHF_2$), trifluoromethyl (—$CF_3$), fluoroethyl (—$CFHCH_3$ or —$CH_2CH_2F$), perfluoroethyl (—$CF_2CF_3$), fluoropropyl (—$CHFCH_2CH_3$ or —$CH_2CHFCH_3$ or —$CH_2CH_2CH_2F$), perfluoropropyl (—$CF_2CF_2CF_3$ or —$CF(CF_2)_2$), chloromethyl (—$CH_2Cl$), dichloromethyl (—$CHCl_2$), trichloromethyl (—$CCl_3$), chloroethyl (—$CClHCH_3$ or —$CH_2CH_2Cl$), perchloroethyl (—$CCl_2CCl_3$), chloropropyl (—$CHClCH_2CH_3$ or —$CH_2CHClCH_3$ or —$CH_2CH_2CH_2Cl$), perchloropropyl (—$CCl_2CCl_2CCl_3$ or —$CCl(CCl_2)_2$), cyano (—CN), aldehyde (—C(O)H), carboxylic acid (—C(O)OH), carboxylate (—$C(O)O^-$), carbomethoxy (—$C(O)OCH_3$), carboethoxy (—$C(O)OCH_2CH_3$), dimethyl amine (—$N(CH_3)_2$), or acid chloride (—C(O)Cl);

$R_2$ is hydrogen (—H), chlorine (—Cl), or fluorine (—F) atom, a group consisting of methyl (—$CH_3$), ethyl (—$CH_2CH_3$), ethylene (—$CHCH_2$), ethyne (—CCH), n-propyl (—$CH_2CH_2CH_3$), iso-propyl (—$CH(CH_3)_2$), cyclopropyl (—$CH(CH_2)_2$), tert-butyl (—$C(CH_3)_3$), propene (—$CHCHCH_3$ or —$CH_2CHCH_2$), cyclopropene (—$CH(CH)_2$ or —$C(CH)CH_2$), propyne (—$CCCH_3$ or —$CH_2CCH$), hydroxyl (—OH), methylalcohol (—$CH_2OH$), ethylalcohol (—$CH_2CH_2OH$ or —$CH(OH)CH_3$), ethyldiol (—$CH(OH)CH_2(OH)$), propanol (—$CH(OH)CH_2CH_3$ or —$CH_2CH(OH)CH_3$ or —$CH_2CH_2CH_2OH$), propandiol (—$CH(OH)CH(OH)CH_3$ or —$CH(OH)CH_2CH_2OH$ or —$CH_2CH(OH)CH_2OH$), methylether (—$OCH_3$), ethylether (—$OCH_2CH_3$), fluoromethyl (—$CH_2F$), difluoromethyl (—$CHF_2$), trifluoromethyl (—$CF_3$), fluoroethyl (—$CFHCH_3$ or —$CH_2CH_2F$), perfluoroethyl (—$CF_2CF_3$), fluoropropyl (—$CHFCH_2CH_3$ or —$CH_2CHFCH_3$ or —$CH_2CH_2CH_2F$), perfluoropropyl (—$CF_2CF_2CF_3$ or —$CF(CF_2)_2$), chloromethyl (—$CH_2Cl$), dichloromethyl (—$CHCl_2$), trichloromethyl (—$CCl_3$), chloroethyl (—$CClHCH_3$ or —$CH_2CH_2Cl$), perchloroethyl (—$CCl_2CCl_3$), chloropropyl (—$CHClCH_2CH_3$ or —$CH_2CHClCH_3$ or —$CH_2CH_2CH_2Cl$), perchloropropyl (—$CCl_2CCl_2CCl_3$ or —$CCl(CCl_2)_2$), cyano (—CN), aldehyde (—C(O)H), carboxylic acid (—C(O)OH), carboxylate (—$C(O)O^-$), carbomethoxy (—$C(O)OCH_3$), carboethoxy (—$C(O)OCH_2CH_3$), dimethyl amine (—$N(CH_3)_2$), or acid chloride (—C(O)Cl);

$R_3$ is hydrogen (—H), chlorine (—Cl), or fluorine (—F) atom, a group consisting of methyl (—$CH_3$), ethyl (—$CH_2CH_3$), ethylene (—$CHCH_2$), ethyne (—CCH), n-propyl (—$CH_2CH_2CH_3$), iso-propyl (—$CH(CH_3)_2$), cyclopropyl (—$CH(CH_2)_2$), tert-butyl (—$C(CH_3)_3$), propene (—$CHCHCH_3$ or —$CH_2CHCH_2$), cyclopropene (—$CH(CH)_2$ or —$C(CH)CH_2$), propyne (—$CCCH_3$ or —$CH_2CCH$), hydroxyl (—OH), methylalcohol (—$CH_2OH$), ethylalcohol (—$CH_2CH_2OH$ or —$CH(OH)CH_3$), ethyldiol (—$CH(OH)CH_2(OH)$), propanol (—$CH(OH)CH_2CH_3$ or —$CH_2CH(OH)CH_3$ or —$CH_2CH_2CH_2OH$), propandiol (—$CH(OH)CH(OH)CH_3$ or —$CH(OH)CH_2CH_2OH$ or —$CH_2CH(OH)CH_2OH$), methylether (—$OCH_3$), ethyl ether (—$OCH_2CH_3$), fluoromethyl (—$CH_2F$), difluoromethyl (—$CHF_2$), trifluoromethyl (—$CF_3$), fluoroethyl (—$CFHCH_3$ or —$CH_2CH_2F$), perfluoroethyl (—$CF_2CF_3$), fluoropropyl (—$CHFCH_2CH_3$ or —$CH_2CHFCH_3$ or —$CH_2CH_2CH_2F$), perfluoropropyl (—$CF_2CF_2CF_3$ or —$CF(CF_2)_2$), chloromethyl (—$CH_2Cl$), dichloromethyl (—$CHCl_2$), trichloromethyl (—$CCl_3$), chloroethyl (—$CClHCH_3$ or —$CH_2CH_2Cl$), perchloroethyl (—$CCl_2CCl_3$), chloropropyl (—$CHClCH_2CH_3$ or —$CH_2CHClCH_3$ or —$CH_2CH_2CH_2Cl$), perchloropropyl (—$CCl_2CCl_2CCl_3$ or —$CCl(CCl_2)_2$), cyano (—CN), aldehyde (—C(O)H), carboxylic acid (—C(O)OH), carboxylate (—$C(O)O^-$), carbomethoxy (—$C(O)OCH_3$), carboethoxy (—$C(O)OCH_2CH_3$), dimethyl amine (—$N(CH_3)_2$), or acid chloride (—C(O)Cl); and $R_4$ is hydrogen (—H), chlorine (—Cl), or fluorine (—F) atom, a group consisting of methyl (—$CH_3$), ethyl (—$CH_2CH_3$), ethylene (—$CHCH_2$), ethyne (—CCH), n-propyl (—$CH_2CH_2CH_3$), iso-propyl (—$CH(CH_3)_2$), cyclopropyl (—$CH(CH_2)_2$), tert-butyl (—$C(CH_3)_3$), propene (—$CHCHCH_3$ or —$CH_2CHCH_2$), cyclopropene (—$CH(CH)_2$ or —$C(CH)CH_2$), propyne (—$CCCH_3$ or —$CH_2CCH$), hydroxyl (—OH), methylalcohol (—$CH_2OH$), ethylalcohol (—$CH_2CH_2OH$ or —$CH(OH)CH_3$), ethyldiol (—$CH(OH)CH_2(OH)$), propanol (—$CH(OH)CH_2CH_3$ or —$CH_2CH(OH)CH_3$ or —$CH_2CH_2CH_2OH$), propandiol (—$CH(OH)CH(OH)CH_3$ or —$CH(OH)CH_2CH_2OH$ or —$CH_2CH(OH)CH_2OH$), methylether (—$OCH_3$), ethylether (—$OCH_2CH_3$), fluoromethyl (—$CH_2F$), difluoromethyl (—$CHF_2$), trifluoromethyl (—$CF_3$), fluoroethyl (—$CFHCH_3$ or —$CH_2CH_2F$), perfluoroethyl (—$CF_2CF_3$), fluoropropyl (—$CHFCH_2CH_3$ or —$CH_2CHFCH_3$ or —$CH_2CH_2CH_2F$), perfluoropropyl (—$CF_2CF_2CF_3$ or —$CF(CF_2)_2$), chloromethyl (—$CH_2Cl$), dichloromethyl (—$CHCl_2$), trichloromethyl (—$CCl_3$), chloroethyl (—$CClHCH_3$ or —$CH_2CH_2Cl$), perchloroethyl (—$CCl_2CO_3$), chloropropyl (—$CHClCH_2CH_3$ or —$CH_2CHClCH_3$ or —$CH_2CH_2CH_2Cl$), perchloropropyl (—$CCl_2CCl_2CCl_3$ or —$CCl(CCl_2)_2$), cyano (—CN), aldehyde (—C(O)H), carboxylate (—$C(O)O^-$), carbomethoxy (—$C(O)OCH_3$), carboethoxy (—$C(O)OCH_2CH_3$), dimethyl amine (—$N(CH_3)_2$), or acid chloride (—C(O)Cl).

2. A method of inhibiting the ethylene response in a plant, said method comprising:

a. applying to a plant a compound of claim 1; and b. exposing the compound of claim 1 on said plant to light.

3. A method of inhibiting the ethylene response in a plant, said method comprising:

a. applying to a plant a compound of claim 1; and b. exposing the compound of claim 1 on said plant to heat.

4. The compound of claim 1 wherein $R_1$ is methyl (—$CH_3$), $R_2$ is hydrogen (—H) $R_3$ is hydrogen (—H) and $R_4$ is hydrogen (—H).

5. The compound of claim 1 wherein $R_1$ is hydrogen (—H), $R_2$ is hydrogen (—H) $R_3$ is hydrogen (—H) and $R_4$ is methyl (—$CH_3$).

6. The compound of claim 1 wherein $R_1$ is trifluoromethyl (—$CF_3$), $R_2$ is hydrogen (—H) $R_3$ is hydrogen (—H) and $R_4$ is hydrogen (—H).

7. The compound of claim 1 wherein $R_1$ is hydrogen (—H), $R_2$ is hydrogen (—H) $R_3$ is hydrogen (—H) and $R_4$ is trifluoromethyl (—$CF_3$).

* * * * *